United States Patent [19]
Suzuki et al.

[11] Patent Number: 5,882,680
[45] Date of Patent: Mar. 16, 1999

[54] SEAMLESS CAPSULE AND METHOD OF MANUFACTURING THE SAME

[75] Inventors: Toshiyuki Suzuki; Masayuki Ikeda; Mamoru Sugiyama, all of Tokyo, Japan

[73] Assignee: Freund Industrial Co., Ltd., Tokyo, Japan

[21] Appl. No.: 757,135

[22] Filed: Dec. 3, 1996

[30] Foreign Application Priority Data

Dec. 7, 1995 [JP] Japan .................................. 7-319313

[51] Int. Cl.$^6$ .................................................. A61K 9/48
[52] U.S. Cl. ........................ 424/451; 424/452; 424/456; 424/457; 424/458
[58] Field of Search .................. 424/451, 452, 424/456, 457, 458

[56] References Cited

U.S. PATENT DOCUMENTS

| | | | |
|---|---|---|---|
| 5,478,508 | 12/1995 | Suzuki et al. | 264/4 |
| 5,500,224 | 3/1996 | Vranckx et al. | 424/451 |
| 5,595,757 | 1/1997 | Kiefer et al. | 424/451 |
| 5,650,232 | 7/1997 | Glenn et al. | 428/402.2 |

FOREIGN PATENT DOCUMENTS

| | | |
|---|---|---|
| 53-39193 | 10/1978 | Japan . |
| 54-92616 | 7/1979 | Japan . |
| 59-190916 | 10/1984 | Japan . |
| 5-68446 | 9/1993 | Japan . |

OTHER PUBLICATIONS

Translation of JP 59–190, 916, Oct. 1984.
Translation of JP 53–39, 139, Oct. 1978.

*Primary Examiner*—David W. Wu
*Attorney, Agent, or Firm*—Kane, Dalsimer, Sullivan, Kurucz, Levy, Eisele and Richard, LLP

[57] ABSTRACT

There are provided a seamless capsule containing therein a large quantity of an active ingredient which is difficultly soluble in water and oil and a method of manufacturing the seamless capsule. Encapsulating liquid 1, in which the active ingredient is difficultly soluble in water and oil is suspended in oil as particles each having the mean particle diameter of less than 20 μm, is enclosed in hydrophilic outer shells. This seamless capsule SC is manufactured in such a manner that from a multiple nozzle 7, suspension, in which the active ingredient which is difficultly soluble in water and oil is dispersed in oil and the active ingredient in thus obtained dispersion is pulverized to obtain particles each having the mean particle diameter of less than 20 μm, as encapsulating liquid 1, and aqueous liquid of a shell forming substance, as outer shell forming liquid 3, are dropped into hardening liquid 10.

5 Claims, 2 Drawing Sheets

SEAMLESS CAPSULE AND METHOD OF MANUFACTURING THE SAME

BACKGROUND OF THE INVENTION

1. Field of the Invention

This invention relates to a seamless capsule, and more particularly to techniques effectively applied to a seamless capsule capable of containing a large quantity of an active ingredient.

2. Statement of the Related Art

In general, hard capsules are employed for filling powdery material. However, with this hard capsules, there are presented the following problems. That is, firstly, the hard capsules are standardized their size and volume, even in a smallest capsule No. 5, the length thereof is as large as 1.2~1.4 cm, and hard capsules smaller than No. 5 can not be produced because of the standard and technical problem. Secondly, during the manufacturing of the capsules, such processes as encapsulating, cap coupling and the like are needed, so that the production efficiency is low. Thirdly, according to Japanese law, in the field of health foods, ingredients, with which the hard capsules are permitted to be encapsulated, are limited, so that types of products permitted to be on sale are limited.

On the other hand, although there are no such problems as described above for a seamless capsule and a soft capsule, such a problem is presented that, even in the case of these capsules, the capsules can not be encapsulated with the powder as it is. Then, there have been tried various methods for encapsulating the seamless capsules and the like with a powder material, which are not limited in dimensions and materials to be encapsulated. In these cases, it is conventional that the powder is dissolved in a solvent medium to provide a liquid solution, or the powder is suspended in a solvent medium to provide a fluid dispersion, which is encapsulated in a capsule.

In this case, as a solvent medium to be used, such one is desirable that a powder material as being an object can be dissolved at a high concentration, a stable solution can be obtained after the dissolution and no harm is given to human body. However, as for a powder material desired to be used, in fact, there are many cases where such a convenient and suitable solvent medium does not exist. Hence, in general, a powder material is enclosed in capsules in a state of a fluid suspension. Then, as techniques for encapsulating a capsule with this suspension, especially encapsulating a seamless capsule to enclose the suspension therein, there have been known several examples as shown in Japanese Patent Application Publication No. 68446/1993, Patent Application Publication No. 39193/1978, Patent Laid-Open No. 190916/1984, Patent Laid-Open No. 92616/1979 and so forth.

Here, in Patent Application Publication No. 68446/1993, there is disclosed a method, in which a stabilizer is added to freeze-dried powder of Lactobacillus bifidus suspended in hydrogenated oil having a melting point between 30° C. and 45° C. and a melting point range of less than 3° C. encapsulated in a soft capsule. In this case, the hydrogenated oil having the small range of the melting point is used, whereby the suspension is hardened immediately, so that moisture in the shell of capsule is prevented from moving to Lactobacillus bifidus. Furthermore, in Patent Application Publication No. 39193/1978, there is disclosed a mononucleus double-wall capsule, whose nuclear portion (inner-most layer) is encapsulated with powder dispersed in oil, which is hardened about at 10° C. With this arrangement, it becomes possible to form a material to provide a capsule, otherwise it should be impossible to form the material to provide a capsule with a seamless one-wall capsule.

Further, in Patent Laid-Open No. 190916/1984, there is disclosed a seamless capsule containing a filler obtained by dispersing in oil an inclusion compound, in which a hydrophilic substance is included in a clathrate inclusion compound. In this case, the hydrophilic substance is to be taken into the interior of cavity formed in the clathrate inclusion compound, an insoluble composite material is formed, and this clathrate inclusion compound is dispersed in oil to obtain a stable dispersion containing the hydrophilic substance, so that a capsule can be formed. On the other hand, in Patent Laid-Open No. 92616/1979, there is disclosed a bioavailability improving drug, in which a solid chemical agent which is difficultly soluble in water is dispersed in oil (at liquid room temperature), with which a seamless mini-capsule having a particle diameter of 1~3 mm is encapsulated.

Here, the inventors of the present invention have found that, when the capsule encapsulating therein the suspension is manufactured, if the fill of the suspension is increased, then, when liquid drops through a multiple nozzle, the outer shells of the capsules are broken and satisfactory capsules can not be formed.

Then, when the above-described conventional methods are examined from the above-described viewpoint, firstly, in Patent Application Publication No. 68446/1993, the hydrogenated oil having the melting point higher than the room temperature is used as encapsulated- in liquid, whereby the suspension is hardened immediately at the time of formation of a capsule, so that an outer shell is difficultly subjected to the influence of the moisture of suspension and no damage is caused to the capsule. However, in this method, the encapsulated liquid is in a solid state at the room temperature, so that all stage of manufacturing the capsule, i.e. preparation, storage and supplying thereof should be performed under heated conditions. For this, the active ingredient is easily deteriorated and the heating means is needed at all times. Further, a solvent medium for dispersion is limited to the hydrogenated oil, there is a case where the active ingredient may be precluded from being absorbed into the human body depending upon the type of the hydrogenated oil, and there is a case where it is not appropriate to apply this method. In addition, the content is hardened at the room temperature, whereby the capsule becomes opaque, so that the product seems ugly, and further, detection of defectives such as uneven shell thickness, damages and the like is difficult. Hence, this method is not used in general.

Next, in Patent Application Publication No. 39193/1978, the encapsulated liquid (nuclear portion) is doubly protected by an intermediate layer (inner layer) and an outer layer,. so that damages are uneasily caused to the outer shell. However, in this method, use of a triple nozzle is essential, so that the device become complicated and it is not easy to perform operational control. Furthermore, the double layered capsule is needed, so that such a disadvantage is presented that the fill of the encapsulated liquid is decreased as compared with a capsule having a particle diameter equal thereto.

Further, in Patent Laid-Open No. 190916/1984, such an arrangement is adopted that the clathrate inclusion compound is dispersed in the oil, whereby, when the quantity of the clathrate inclusion compound is increased, a problem of the outer shell damage is still presented. Furthermore, the active ingredient is limited to the hydrophilic substance, and it is necessary to add the inclusion material such as cyclodextrin by more than a quantity equal thereto. Accordingly, such a problem is presented that the types of the active ingredient to be used are limited, and further, the content of the active ingredient is also restricted. Furthermore, it takes much process to produce the clathrate inclusion compound, and further, the production efficiency is low.

On the other hand, in Patent Laid-Open No. 92616/1979, as the encapsulated liquid, there is used the active ingredient difficultly soluble in water to be molecularly dispersed (dissolved) and/or particulately dispersed and, as for the outer shell damage, conditions equal thereto are brought about. Further, in this case, only the one obtained by dissolution is described as an example, but, there is not described the embodiment of forming the capsule for the one dispersed particulately.

Then, the inventors of the present invention, paying their attention to the technique described in this Patent Laid-Open No. 92616/1979, have tried to form the capsule containing the encapsulated liquid not described in the example, in which the active ingredient is dispersed particulately. As the result, they have been confronted with the fact that, when it is tried to increase the containing ratio of the active ingredient, the outer shell breakage are often caused.

SUMMARY OF THE INVENTION

It is an object of the present invention to provide a seamless capsule containing a large quantity of an active ingredient difficultly soluble (including "insoluble") both in water and oil and a method of manufacturing the same.

The above-described and other objects, and novel features will be readily apparent from the description of this specification and the accompanying drawings.

The following is the brief description of the outline of the typical invention out of the inventions disclosed in the present application.

The inventors of the present invention have found the fact that the mean particle diameter of the active ingredient suspended in the oil relates to the occurrence of the damages as the result of the research relating to the causes of the damages of the outer shells due to the increase in the fill of the suspension as described above. Then, it has been found that if this mean particle diameter is less than 20 $\mu$m, then the outer shells can be free from damages, and the products having more fill of the active ingredient can be produced. Then, it has been found that the active ingredient is made to be the suspension having the mean particle diameter of less than 20 $\mu$m, so that the active ingredient can be contained even in the outer shells and the fill of the active ingredient can be further increased, and, in order to manufacture the above-described suspension, it is desirable to subject the active ingredient to the wet pulverizing in the respective solvent medium for dispersion.

Then, the seamless capsule according to the present invention is characterized in that liquid, in which the active ingredient which is difficultly soluble in water and oil is suspended in oil as particles each having the mean particle diameter of less than 20 $\mu$m, is encapsulated in a hydrophilic outer shell. In this case, it is desirable that the particles are formed by the active ingredient being subjected to the wet pulverizing in oil.

Furthermore, the above-described active ingredient may be encapsulated in the above-described outer shell as the particles each having the mean particle diameter of less than 20 $\mu$m. In this case also, it is desirable that the particles in the outer shell is formed such that the above-described active ingredient is subjected to the wet pulverizing in water.

On the other hand, the method of manufacturing the seamless capsule according to the present invention is a method, in which liquid drops each having a plurality of layers are dropped though a concentric multiple nozzle into hardening liquid to thereby manufacture the seamless capsules, and is characterized in that there is supplied the suspension, as an inner-most layer liquid of the above-described liquid drops, in which the active ingredient which is difficultly soluble in water and oil is dispersed in oil and the active ingredient in thus obtained dispersion is pulverized to obtain particles each having the mean particle diameter of less than 20 $\mu$m by a wet pulverizing device, and there is supplied an aqueous solution of a shell forming substance as an outer-most layer liquid of the above-described liquid drops.

In this case, the aqueous solution of the above-described shell forming substance may contain the suspension, in which the above-described active ingredient is dispersed in water and the active ingredient in thus obtained dispersion is pulverized to obtain particles each having the mean particle diameter of less than 20 $\mu$m. Furthermore, a high pressure homogenizer may be used as the above-described wet pulverizing device.

DESCRIPTION OF THE PREFERRED EMBODIMENT

Detailed description will hereunder be given of an embodiment of the present invention with reference to the drawings.

Figure 1:
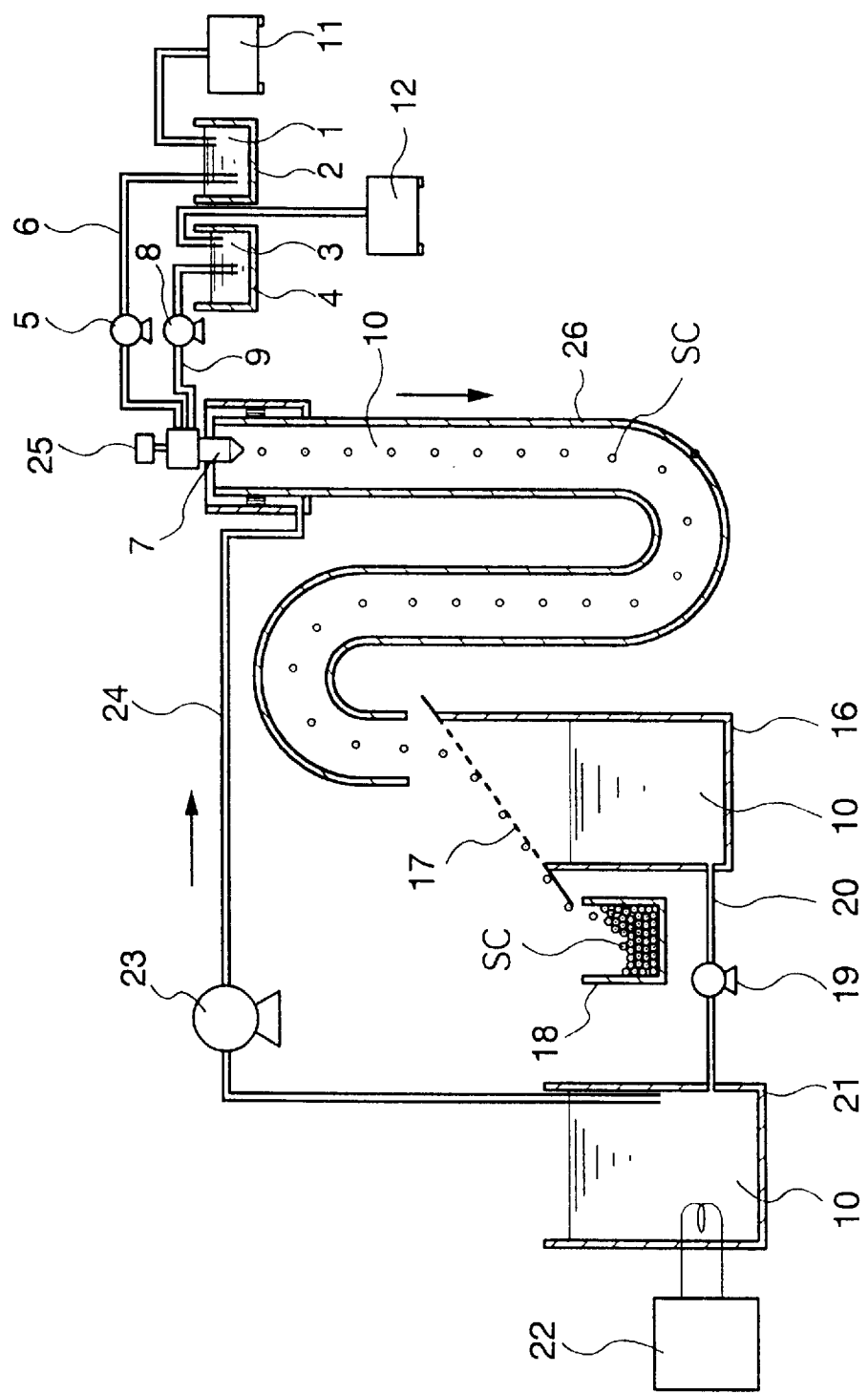
FIG. 1 shows the arrangement of a device for manufacturing a seamless capsule used for carrying out the method of manufacturing a seamless capsule according to the present invention.

FIG. 1 shows the arrangement of a device for manufacturing a seamless capsule according to the present invention, and a method of manufacturing a seamless capsule according to the present invention is carried out by this device. Furthermore, FIG. 2 enlargedly shows the arrangement of a nozzle portion of the device for manufacturing a seamless capsule as shown in FIG. 1.

The seamless capsule according to the present invention is a seamless capsule, in which encapsulating liquid 1, in which an active ingredient is suspended in oil as particles each having the mean particle diameter of less than 20 $\mu$m, is enclosed by a hydrophilic outer shell 28. This seamless capsule is one, in which the quantity of the active ingredient contained in a particle is large as compared with the conventional seamless capsules. Furthermore, in this seamless capsule, the active ingredient can be contained even in the outer shell 28; so that the quantity of the active ingredient in one capsule can be further increased.

Figure 2:
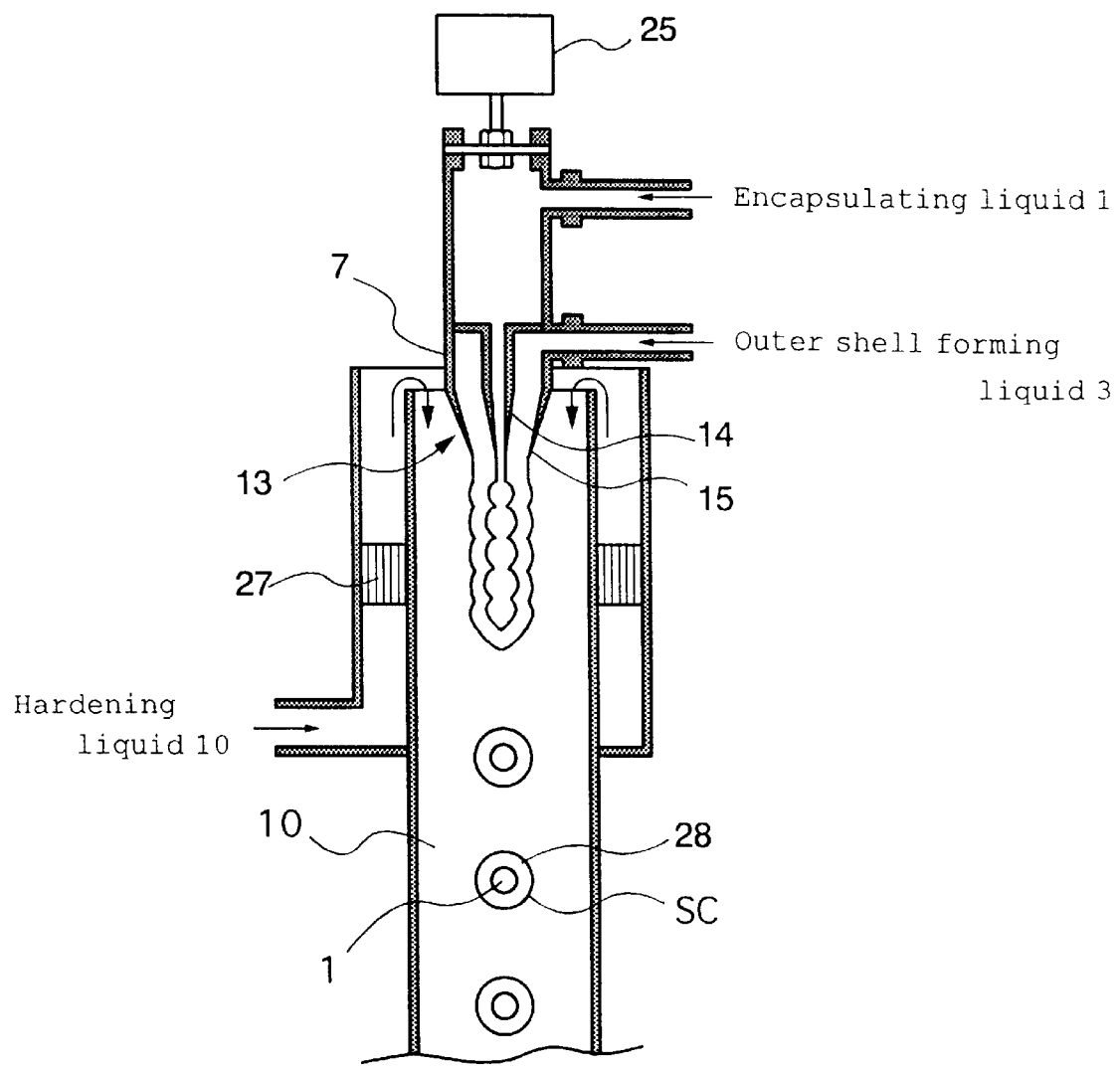
FIG. 2 is an enlarged sectional view showing the outline of the arrangement of a nozzle portion of the device for manufacturing a seamless capsule shown in FIG. 1.

Firstly, description will given of the device for manufacturing a seamless capsule in order to manufacture the seamless capsule according to the present invention. This device for manufacturing a seamless capsule is a device of a so-called nozzle-in liquid type, in which liquid drops each having a plurality of layers are dropped into hardening liquid 10 to thereby manufacture a seamless capsule SC as shown in FIGS. 1 and 2. A liquid drop flow-out portion 13 thereof is a concentric multiple nozzle having a double-layered orifice construction as shown in FIG. 2.

In the device for manufacturing a seamless capsule as shown in FIG. 1, the encapsulating liquid (the inner-most layer liquid) 1 for forming the seamless capsule SC is manufactured by a wet pulverizing device 11 and stored in a tank 2 for encapsulating liquid. Furthermore, an outer shell forming liquid (the outer-most layer liquid) 3 for forming an outer shell for covering the encapsulating liquid 1 is manufactured by a wet pulverizing device 12 and stored in a tank 4 for outer shell forming liquid. Then, the encapsulating liquid 1 is supplied under pressure to a multiple nozzle 7 having a double-layered orifice through a piping 6 from the tank 2 for the encapsulating liquid by a pump 5, and the outer shell forming liquid 3 is supplied under pressure to the above-described multiple nozzle 7 through a piping 9 from the tank 4 for the outer shell forming liquid by a pump 8.

Here, in the device for manufacturing a seamless capsule in this embodiment, as the encapsulating liquid 1, there is used the suspension, in which the active ingredient consisting of a substance which is difficultly soluble (including "insoluble") both in water and oil is contained as suspended particles each having the mean particle diameter of less than 20 $\mu$m.

Incidentally, in the present application, the term "difficultly soluble" means an extent where the total quantity is not soluble in oil and suspended particles are left behind, and, for example, the extent means an extent where the solubility is less than 10 g/100 ml, i.e., nearly the extent of being indicated as "sparingly soluble" according to the Japanese pharmacopoeia, or therebelow. Furthermore, the term "the active ingredient" means a ingredient for displaying a purpose for use, functions, performances and the like of a capsule to be manufactured, and, as described above, the active ingredient maybe a solid material which is difficultly soluble in water and oil. Materials included in a wide range, which can be utilized as a medicine, a quasi-drug ingredient, a cosmetic, a food stuff, an agricultural chemicals and the like, are selected as the objects.

On the other hand, as oil used as the encapsulating liquid 1, there are listed fats, oils and other fatty ester having glycerin ester as the main ingredient, such as animal fats and oils, and vegetable oil, and further, hydrocarbon, aliphatic alcohol, fatty acid and the like, which are substantially insoluble in water and liquid state at the room temperature. Incidentally, the concentration of the active ingredient of the encapsulating liquid 1 is respectively different depending upon the purpose and the physical properties such as the viscosity of the suspension. However, normally, the range is limited to 1~60 weight %.

Further, in the present invention, the reason why the mean particle diameter of the active ingredient is set at a value of less than 20 $\mu$m resides in that, when the mean particle diameter is larger than it, not only the above-described damages occur, but also it serves as the cause of malfunctions of a gear pump for supplying the encapsulating liquid 1, and, in the extreme case, the pump is stopped. Furthermore, when the mean particle diameter is large, there are presented such problems that deviation of the amount of the active ingredient per product (capsule) enlarged and poor appearance due to the sedimentation of the suspension in the capsule.

In this embodiment, the powder of the active ingredient is agitated and dispersed in oil, and thereafter, a process of forming the suspension is carried out by the wet pulverizing device 11, so that the above-described suspension of encapsulating liquid 1 can be manufactured. In this case, such a method may be adopted that the active ingredient is previously formed to provide particles each having the mean particle diameter of less than 20 $\mu$m, and the pulverized active ingredient is agitated and dispersed in oil to produce the suspension. However, it is difficult to completely unfasten the aggregate of pulverizing particles. It is more reliable that the active ingredient is pulverized in situ in a solvent to thereby obtain the suspension.

As the wet pulverizing devices 11, there may be adopted any one of a high pressure homogenizer, a colloid mill, a planetary ball mill, a vibrating ball mill, an ultrasonic homogenizer and so forth, only if they can process the active ingredient to provide particles each having the mean particle diameter of less than 20 $\mu$m. However, the high pressure homogenizer is the best as a view point of the pulverizing performance, and elimination of contamination of impurities due to the wear of the device. By the way, the high pressure homogenizer is constructed such that two streams of liquid applied thereto with the atmospheric pressure amounting from several hundreds to several thousands are blown out of two mutually opposing narrow flow paths and impinged against each other and the particles are pulverized, dispersed and suspended (emulsified) by the combined actions of impacts, shearing and cavitation, and is put on the market under trade names of a "Nanomizer", "Microfluidizer" and so forth.

Next, the outer shell forming liquid 3, there are used hydrophilic high molecular substance such as gelatin, agar-agar, alginate, pectin and the like as the main ingredients, a plasticizer and a coloring material are suitably added thereto, and, during the manufacturing the seamless capsules, the outer shell forming liquid is supplied as an aqueous liquid. Incidentally, it is needless to say that the outer shell 28 is insoluble in the hardening liquid 10 and is solidified in the hardening liquid 10.

Here, there has heretofore been presented such a problem that, when the active ingredient is contained in the outer shells in order to increase the quantity of the active ingredient, damages of the outer shells take place as described above at the time of formation of a capsule, and the dispersion becomes uneven. However, according to the experiments carried out by the inventors of the present invention, it has been found that, if the active ingredient is contained in the outer shells in the state of the particles each having the mean particle diameter of less than 20 $\mu$m, then no damages takes place and the uniformity of the capsules become satisfactory. Then, in this embodiment, in this outer shell forming liquid 3, the active ingredient is contained in the state of the particles each having the mean particle diameter of less than 20 $\mu$m similarly to the encapsulating liquid 1, so that, in each of the seamless capsules, the active ingredient as much as possible is contained. That is, the outer shell forming liquid 3 is produced in such a manner that the active ingredient is dispersed in water and subjected to the wet pulverizing by the wet pulverizing device 12 as described above and a ingredient for the shell forming is added thereto. In manufacturing the outer shell forming liquid 3, it is possible that the wet pulverizing is carried out after the active ingredient is dispersed in the aqueous liquid of the ingredient for forming the outer shell. Furthermore, the reason why the mean particle diameter less than 20 $\mu$m is adopted resides in obtaining the stability of the outer shell and keeping the steady operation of the gear pump similarly to the above description.

Now, the device for manufacturing a seamless capsule in this embodiment is of a nozzle-in-liquid type shown in FIG. 2 as described above, and a multiple nozzle 7 having a double-layered orifice construction is inserted into an inlet portion of a main flowpath piping 26. This main flowpath piping 26 is supplied with the hardening liquid 10 through equalizer 27. Accordingly, the outlet portion of the multiple nozzle 7 is constantly immersed in the hardening liquid 10. Then, the encapsulating liquid 1 and the outer shell forming liquid 3 are blown out through the double-layered orifice into the hardening liquid 10, and the liquid drops each having the plurality of layers are dropped into the hardening liquid 10 in the state where the liquid 3 covers the total surrounding of the liquid 1. That is, in this embodiment, the encapsulating liquid 1 through a central nozzle 14 of the multiple nozzle 7 and the outer shell forming liquid 3 through an outer nozzle 15 are blown out into the hardening liquid 10, respectively. Incidentally, it is possible to form the multiple nozzle 7 to provide a multiple nozzle having a triple or more paths. In this case, as a result, a seamless capsule having a further more intermediate layer is formed.

Furthermore, in this embodiment, the multiple nozzle 7 is vibrated by a vibrating device 25. Accordingly the encapsulating liquid 1 and the outer shell forming liquid 3, which are blown out of the multiple nozzle 7, are formed to provide multi-layer liquid drops by the vibrations given to the multiple nozzle 7 by the vibrating device 25 in the hardening liquid 10 in the main flowpath piping 26. Then, as the encapsulating liquid 1 and the outer shell forming liquid 3 flow through the main flowpath piping 26, they are hardened by the action of the hardening liquid 10, and formed to provide the seamless capsules SC. With this arrangement, the encapsulating liquid 1, in which the active ingredient is suspended in oil in the state of the particles each having the mean particle diameter of less than 20 μm, is encapsulated by the hydrophilic outer shell 28 and the active ingredient is contained even in the outer shells, to thereby complete the seamless capsule SC.

Thus formed seamless capsule SC flows together with the hardening liquid 10 from an outlet end of the main flowpath piping 26 onto an inclined porous body 17 of a separating tank 16. Then, immediately after separated from the hardening liquid 10 on the inclined porous body 17, the seamless capsule SC rolls down on the slope of the inclined porous body 17 and recovered into a product recovery container 18. Thereafter, thus finished capsules are dried, so that products can be finished. In this case, coatings such as an enteric film, a sustained release film, sugar-coating or the like may be applied onto the finished seamless capsules, or it is possible that any other active ingredient may be coated on the seamless capsule SC as being the core.

Incidentally, in this embodiment, the hardening liquid 10 in the separating tank 16 is delivered under pressure through a piping 20 to a cooling tank 21 by a pump 19. The hardening liquid 10 in the cooling tank 21 is cooled by a cooler 22 to a predetermined temperature, and thereafter, returned into the main flowpath piping 26 through a piping 24 by a pump 23.

As described above, in the seamless capsule SC according to the present invention, even if the quantity of the active ingredient in the encapsulating liquid 1 is increased, not only the quantity of the active ingredient contained in a single seamless capsule can be increased as compared with that in the prior art without damaging the outer shells 28 during the manufacturing of the seamless. capsules, but also the active ingredient can be contained in the outer shell 28, so that the quantity of the active ingredient in each of the seamless capsules can be further increased.

Description will hereunder be given of the results of the experiments of the manufacture of the seamless capsules according to the above-described method.

EXAMPLE 1

Crystal of β-carotene 75 g was added to MCT (middle chain length fatty acid trigliceride) 425 g, and preparatory dispersion was carried out for five minutes at a speed of 10,000 RPM by use of a high-speed agitating type emulsifying-dispersing machine (manufactured by Tokushu-Kikai-Kogyo Co., Ltd.) (The liquid produced after this process is referred to as "dispersion".).

This dispersion was processed three times at 100 MPa (about 1,000 atmospheric pressure) by use of a high pressure homogenizer "Nanomizer LA 33"(manufactured by Nanomizer Co., Ltd.) and suspension was obtained. In this case, the mean particle diameter of β-carotene in the dispersion was 23.1 μm and that of the suspension was 8.3 μm.

Next, in a device for manufacturing a seamless capsule "Spherex"(manufactured by Freund Industrial Co., Ltd.), the suspension heated to 35° C. as the encapsulating liquid and the aqueous solution of 18 wt % gelatin and 2 wt % sorbitol heated to 70° C. as the outer shell forming liquid were dropped at a speed of 20 pieces/sec into the hardening liquid of MCT cooled to 9° C., to thereby manufacture the seamless capsules each having the diameter of 4.0 mm and the shell ratio to total capsule of 20%. In this case, formation of the capsules was smoothly carried out, so that the satisfactory seamless capsules each containing β-carotene of 120 mg/g were obtained.

COMPARATIVE EXAMPLE 1

The dispersion same as that of the Example 1 was used to manufacture the seamless capsules under the same conditions as the Example 1 by use of the "Spherex". In this case, damages of the outer shells occurred in a large percentage during the dropping. Then, in order to prevent such damages from occurring, it was necessary to lower the concentration of dispersion of β-carotene to less than 8 wt %, i.e., β-carotene in the seamless capsule is lowered to less than 64 mg/g.

EXAMPLE 2

Liquid, in which crystal of Nifedipine 200 g was added to MCT 300 g, was used to manufacture, the same process as in the Example 1 was carried out and an oily suspension was manufactured. However, the pressure during the process by use of "Nanomizer LA 33" was set at 150 MPa. In this case, the mean particle diameters of Nifedipine were 34.8 μm in the dispersion and 10.2 μm in the suspension.

Separately of this, liquid, in which crystal of Nifedipine 75 g was added to water 425 g, was processed for 60 min. at a speed of 8,000 RPM by use of "TK Homomixer" for preparatory dispersion. This dispersion was processed three times at 100 MPa by use of "Nanomizer LA33" to thereby obtain the suspension. The mean particle diameter of Nifedipine in this suspension was 4.2 μm. Gelatin and sorbitol were added to this suspension, heated and dissolved to obtain the aqueous liquid containing therein 10.4 wt % Nifedipine, 18.0 wt % Gelatin and 2.0 wt % Sorbitol.

Then, in the same device as in the Example 1, the oily suspension being at the room temperature as the encapsulating liquid and the aforesaid aqueous liquid being at 56° C. as the outer shell forming liquid were dropped into the hardening liquid of MCT cooled to 10° C. , to thereby manufacture the seamless capsules each having the diameter of 1.5 mm and the shell ratio of 50%. In this case, formation of the capsules was carried out smoothly and the satisfactory seamless capsules having Nifedipine 371 mg/g.

COMPARATIVE EXAMPLE 2

In the Example 2, the oily dispersion prior to the processing by use of "Nanomizer LA33" was made to be the encapsulating liquid, and the liquid having the same composition as the outer shell forming liquid used in the Example 2, except for that Nifedipine was not dispersed, was used as the outer shell forming liquid to thereby manufacture the seamless capsules under the same conditions as in the Example 2.

In this case, the capsules were damaged during the dropping and no satisfactory capsules were obtained at all. Then, in order to prevent such damages, it was necessary to make the concentration of Nifedipine in the encapsulating liquid to be less than 20 wt %.

Nifedipine was encapsulated as a solution state, and the solution was made by dissolving Nifedipine in Polyethylene glycol 400; the well known practice. However, in this case, the concentration of Nifedipine was limited to 8 wt % from the solubility.

As has been described hereinabove, detailed description has been given of the invention invented by the inventors of the present invention with reference to the embodiment. However, the present invention should not necessarily be limited to the above-described embodiment, and it is needless to say that the present invention can be modified variously within the scope not departing from the gist thereof.

For example, the type and fill of the active ingredient should not necessarily be limited to those in the above-described examples. Furthermore, the method of suspending should not necessarily be limited to the above-described method and various methods using other devices are applicable. Further, it is possible to suitably add a stabilizer, plasticizer, seasoning matter, coloring matter, spicing matter, pigment, preserving matter and the like in addition to the active ingredient.

On the other hand, in the above-described Example 2, the active ingredient is contained in the outer shell forming liquid 3 to thereby form the outer shell 28 containing the active ingredient. However, it is needless to say that it is also possible to use the ordinary outer shell not containing the active ingredient in particular, to thereby enclose the encapsulating liquid 1 according to the present invention.

In the above description, there has been described the invention invented by the inventors of the present invention in the case where the invention is applied to the seamless capsule and the method of manufacturing the same in the field of utilization. However, the present invention should not necessarily be limited to this. Furthermore, the seamless capsules according to the present invention are usable in various applications such as cosmetic goods, intermediate products for cosmetic goods, foods for medical use, health foods, intermediate products for foods, agricultural chemicals, additional matters for animal feeding stuff and the like in addition to medicines, intermediate products for medical use, quai-drug ingredients and toiletry goods.

The followings are the briefly described effects to be obtained by the typical invention out of the inventions disclosed in the present application.

(1) The mean particle diameter of the active ingredient of the encapsulating liquid is made to be less than 20 $\mu$m, whereby, even if the fill of the active ingredient of the encapsulating liquid is increased, there is such an advantage that the outer shells are not damaged during the manufacturing of the capsules. Accordingly, it becomes possible to increase the quantity of the active ingredient contained in one capsule as compared with that in the prior art.

(2) The mean particle diameter of the active ingredient is made to be less than 20 $\mu$m, whereby, even if the active ingredient is contained in the outer shell forming liquid, the outer shells will not be damaged and the dispersion will not be uneven and it becomes possible to form the capsules containing the active ingredient in the outer shells too. Accordingly, the quantity of the active ingredient contained in one capsule can be further increased as compared with that in the prior art.

What is claimed is:

1. A seamless capsule, wherein liquid, in which an active ingredient is suspended in oil as particles each having a mean particle diameter of less than 20 $\mu$m, is encapsulated in a hydrophilic outer shell, said active ingredient having a solubility in water and oil of less than 10 g/100 ml.

2. A seamless capsule as set forth in claim 1, wherein said particles are formed by wet-pulverizing said active ingredient in oil.

3. A seamless capsule as set forth in claim 1, wherein said active ingredient is contained in said outer shell as particles each having the mean particle diameter of less than 20 $\mu$m.

4. A seamless capsule as set forth in claim 3, wherein the particles of said outer shell are formed by wet-pulverizing said active ingredient in water.

5. A seamless capsule as set forth in claim 2, wherein said active ingredient is contained in said outer shell as particles each having the mean particle diameter of less than 20 $\mu$m.

* * * * *